US008709413B2

(12) United States Patent
Simon

(10) Patent No.: US 8,709,413 B2
(45) Date of Patent: Apr. 29, 2014

(54) TREATMENT OF CELIAC DISEASE WITH IGA

(76) Inventor: Michael R. Simon, Ann Arbor, MI (US)

( * ) Notice: Subject to any disclaimer, the term of this patent is extended or adjusted under 35 U.S.C. 154(b) by 0 days.

(21) Appl. No.: 13/214,952

(22) Filed: Aug. 22, 2011

(65) Prior Publication Data

US 2011/0305753 A1 Dec. 15, 2011

Related U.S. Application Data

(63) Continuation-in-part of application No. 12/138,758, filed on Jun. 13, 2008, now Pat. No. 8,021,645, which is a continuation-in-part of application No. 11/851,606, filed on Sep. 7, 2007, now Pat. No. 7,794,721, which is a continuation-in-part of application No. 11/839,781, filed on Aug. 16, 2007, now Pat. No. 7,597,891, which is a continuation-in-part of application No. 11/610,154, filed on Dec. 13, 2006, now abandoned.

(51) Int. Cl.
*A61K 39/395* (2006.01)
(52) U.S. Cl.
USPC .................... 424/130.1; 424/141.1
(58) Field of Classification Search
None
See application file for complete search history.

(56) References Cited

FOREIGN PATENT DOCUMENTS

WO  WO 03/015817    * 2/2003  .......... A61K 39/395
WO  WO 2009/139624 A1 * 11/2009 ............. C07K 16/04

OTHER PUBLICATIONS

Casswall et al. 'Oral IgA-IgG treatment of chronic non-specific diarrhoea in infants and children.' Acta Pediatrica 85(9):1126-1128, 1996.*
Cant et al. 'Egg and cows' milk hypersensitivity in exclusively breast fed infants with eczema, and detection of egg protein in breast milk. British Medical Journal 291:932-935, 1985.*
Weaver et al. Human milk IgA concentrations during the first year of lactation. Arch. Dis. Chil. 78:235-239, 1998.*
Karlsson et al. 'Allergen-responsive CD4 CD25 Regulatory T Cells in Children who Have Outgrown Cow's Milk Allergy.' J. Exp. Med. 199(12):1679-1688, 2004.*
El-Loly et al. 'Bovine Milk Immunoglobulins in Relation to Human Health.' Inter. J. Dairy Sci. 2(3):183-195, 2007.*
Alfred E. Bacon III et al., Immunoglobulin G Directed Against Toxins A and B of *Clostridium difficile* in the General Population and Patients With Antibiotic-Associated Diarrhea; 1994; pp. 205-209; DIAGN Microbiol Infect Dis.
L.A. Barroso et al.; Nucleotide Sequence of *Clostridium difficile* Toxin B Gene; Nucleic Acids Research, vol. 18, No. 13; 1990; Oxford University Press.

Jay A. Berzofsky, et al., Antigen-Antibody Interactions and Monoclonal Antibodies; Fundamental Immunology, Third Edition; 1993; pp. 421, 455-464; Raven Press Ltd., New York.
Mary Boesman-Finkelstein, et al.; Bovine Lactogenic Immunity Against Cholera Toxin-Related Enterotoxins and Vibrio Cholerae Outer Membranes; Infection and Immunity; 1989; pp. 1227-1234; American Society for Microbiology.
Harald Brussow et al., Bovine Milk Immunoglobulins for Passive Immunity to Infantile Rotavirus Gastroenteritis; Journal of Clinical Microbiology, Jun. 1987; pp. 982-986; American Society for Microbiology.
Lawrence A. Cone, MD et al., A Durable Response to Relapsing *Clostridium difficile* Colitis May Require Combined Therapy with High-dose Oral Vancomycin and Intravenous Immune Globulin; Infectious Diseases in Clinical Practice; vol. 4, No. 4, 2007; pp. 217-220.
B. Corthesy; Recombinant Secretory IGA for Immunie Intervention Against Mucosal Pathogens; Immunoglobulins and Mechanisms of Mucosal Immunity; Biochem Soc Trans; 1997; 471-475.
G. Corthier et al.; Emergence in Gnotobiotic Mice of Nontoxinogenic Clones of *Clostridium difficile* from a Toxinogenic One Infection and Immunity, Jun. 1988; pp. 1500-1504; vol. 56, No. 6.
G. Corthier et al.; Protection Against Experimental *Pseudomembranous colitis* in Gnotobiotic Mice by Use of Monoclonal Antibodies Against *Clostridium difficile* Toxin A; Infection and Immunity, Mar. 1991; pp. 1192-1195; vol. 59, No. 3.
Pascal Crottet et al; Expression, Purification and Biochemical Characterization of Recombinant Murine Secretory Component: A Novel Tool in Mucosal Immunology; Biochem Society J; 1999; pp. 299-306.
C.H. Dove et al.; Molecular Characterization of the *Clostridium difficile* Toxin A Gene; Infection and Immunity; Feb. 1990; pp. 480-488; vol. 58, No. 2.
Marion Enrich et al.; Production of *Clostridium difficile* Antitoxin; Infection and Immunity; Jun. 1980; pp. 1041-1043; vol. 28, No. 3.
Ronald Fayer et al.; Immunotherapeutic Efficacy of Bovine Colostral Immunoglobulins from a Hyperimmunized Cow against *Cryptosporidiosis* in Neonatal Mice; Infection and Immunity, Sep. 1990; pp. 2962-2965; vol. 58, No. 9.
Dale N. Gerding; *Clostridium difficile*-Associated Diarrhea and Colitis in Adults; A Prospective Case-Controlled Epidemilogic Study; Arch Intern Med; vol. 146, Jan. 1986.
Helmut Hilpert et al.; Use of Bovine Mild Concentrate Containing Antibody to Rotavirus to Treat Rotavirus Gastroenteritis in Infants; The Journal of Infectious Diseases; vol. 156, No. 1; Jul. 1987; pp. 158-166.
Robert M.L. Jones et al.; Thiol-Disulfide Redox Buffers Maintain a Structure of Immunoglobulin a that is Essential for Optimal in Vitro Binding to Secretory Component; Biochimica et Biophysica; 1998; pp. 265-274.

(Continued)

*Primary Examiner* — Nora Rooney
(74) *Attorney, Agent, or Firm* — Blue Filament Law PLLC; Avery N. Goldstein

(57) ABSTRACT

A process is provided for inhibiting symptoms of food allergy or food intolerance in a subject that includes the oral administration to the subject suffering from food allergy or food intolerance an IgA or an IgM. When administered in a therapeutic quantity based on the subject characteristics and the type of IgA or IgM, symptoms of food allergy or food intolerance in that subject are inhibited. Even non-secretory forms of IgA and IgM are effective when administered orally.

19 Claims, No Drawings

(56) References Cited

OTHER PUBLICATIONS

Ciaran P. Kelly et al; *Clostridium difficile* Colitis; NEJM—*Clostridium difficile* Colitis; pp. 1-17, 1994.

Ciaran P. Kelly et al.; Human Colonic Aspirates Containing Immunoglobulin a Antibody to *Clostridium difficile* Toxin A Inhibit Toxin A—Receptor Binding; 1992; The American Gastroenterological Association; pp. 35-40.

Donald Y.M. Leung et al; Treatment with Intravenously Administered Gamma Globulin of Chronic Relapsing Colitis Induced by *Clostridium difficile* Toxin; From the Division of Pediatric Allergy-Immunology; pp. 633-637, J. Pediatr 118:633-637, 1991.

Jeffrey M. Libby et al; Effects of the Two Toxins of *Clostridium difficile* in Antibiotic-Associated Cecitis in Hamsters; Infection and Immunity; May 1982; pp. 822-829.

Aldo A.M. Lima et al.; Effects of *Clostridium difficile* Toxins a and B in Rabbit Small and Large Intestine in Vivo and on Cultured Cells In Vitro; Infection and Immunity; Mar. 1988; pp. 582-588; vol. 56, No. 3.

Thomas J. Louie et al.; Tolevamer, a Novel Nonantibiotic Polymer, Compared with Vancomycin in the Treatment of Mild to Moderately Sever *Clostridium difficile*-Associated Diarrhea; Clinical Infectious Diseases; 2006; pp. 411-420.

Elke Lullau et al; Antigen Binding Properties of Purified Immunoglobulin A and Reconstituted Secretory Immunoglobulin A Antibodies; The Journal of Biological Chemistry; pp. 16300-16309, 1996.

David M. Lyerly et al.; *Clostridium difficile*: Its Disease and Toxins; Clinical Microbiology Review, Jan. 1988; pp. 1-18.

David M. Lyerly et al.; Characterization of Toxins A and B of *Clostridium difficile* with Monoclonal Antibodies; Infection and Immunity, Oct. 1986; pp. 70-76; vol. 54, No. 1.

David M. Lyerly et al.; Passive Immunization of Hamsters against Disease Caused by *Clostridium difficile* by Use of Bovine Immunoglobulin G Concentrate; Infection and Immunity, Jun. 1991; pp. 2215-2218; vol. 59, No. 6.

D.M. Lyerly et al.; Biological Activities of Toxins A and B of *Clostridium difficile*; Infection and Immunity Mar. 1982; pp. 1147-1150.

David M. Lyerly et al.; Effects of *Clostridium difficile* Toxins Given Intragastrically to Animals; Infection and Immunity Feb. 1985; pp. 349-352; vol. 47; No. 2.

S. Mahe et al; Effect of Various Diets on Toxin Production by Two Strains of *Clostridium difficile* in Gnotobiotic Mice; Infection and Immunity, Aug. 1987; pp. 1801-1805; vol. 55, No. 8.

Ramon D. Martinez et al.; Purification and Charcterization of *Clostridium sordellii* Hemorrhagic Toxin and Cross-Reactivity with *Clostridium difficile* Toxin A (Enterotoxin) Infection and Immunity; May 1988; pp. 1215-1221; vol. 56, No. 5.

Lynne V. McFarland et al.; Nosocomial Acquistion of *Clostridium difficile* infection; The New England Journal of Medicine; pp. 204-210, 1989.

Lynne V. McFarland et al; Review of *Clostridium difficile*-Associated Disease; American Journal of Infection Control; vol. 14, No. 3; Jun. 1986; pp. 99-109.

Stuart McPherson et al; Intravenous Immunoglobulin for the Treatment of Severe, Refractory, and Recurrent *Clostridium difficile* Diarrhea; Disease of the Colon & Rectum; The American Socity of Colon and Rectal Surgeons; pp. 640-645, 2006.

C. Mietens et al; Treatment of Infantile *E. coli* Gastroenteritis With Specific Bovine Anti-*E. coli* Milk Immunoglobulins; European Journal of Pediatrics; 1979; pp. 239-252.

T. J. Mitchell et al; Effect of Toxin A and B of Clostridium Difficile on Rabbit Ileum and Colon; Gut, 1986; pp. 78-85.

Charalabos Pothoulakis et al; Characterization of Rabbit Ileal Receptors for *Clostridium difficile* Toxin A; Evidence for a Receptor-Coupled G Protein; Ileal Receptor for Toxin A; pp. 119-125, 1991.

Sara W. Rothman et al; Differential Cytotoxic Effects of Toxins a and B Isolated From *Clostridium difficile*; Infection and Immunity; Nov. 1984; pp. 324-331.

Jindrich Symersky et al; Expression of the Recombinant Human Immunoglobulin J Chain in *Escherichia coli*; 2000; Molecular Immunology; pp. 133-140.

Carol O. Tacket et al; Protection by Milk Immunoglobulin Concentrate Against Oral Challenge With Enterotoxigenic *Eschericia coli*; the New England Journal of Medicine; May 1988; pp. 1240-1243.

J. Salcedo et al; Intravenous Immunoglobulin Therapy for Severe *Clostridium difficile* Colitis; gut.bmj.com; Dec. 2006; pp. 366-370.

Kenneth D. Tucker et al; Toxin A of *Clostridium difficile* Is a Potent Cytotoxin; Journal of Clinical Microbiology; pp. 869-871; vol. 28, No. 5, 1990.

R. Weltzin et al; Intranasal Monoclonal IGA Antibody to Respiratory Synctial Virus Protects Rhesus Monkeys Against Upper and Lower Respiratory Tract Infection; pp. 256-261.

Richard Weltzin et al; Intranasal Monoclonal Immunoglobulin A Against Respiratory Syncytial Virus Protects Against Upper and Lower Respiratory Tract Infections in Mice; Antimicrobial Agents and Chemotherapy; Dec. 1994; pp. 2785-2791, 1994.

Y. Yoshiyama et al; Specific Antibodies to Cholera Toxin in Rabbit Milk Are Protective Against Vibrio Cholerae-Induced Intestinal Secretion; Immunology; 1987; pp. 543-547.

L.A. Barroso et al; Nucleotide Sequence of *Clostridium difficile* Toxin B Gene; Nucleic Acids Research, vol. 18, No. 13; pp. 4004, 1990.

Stuart Johnson et al; Selective Neutralization of a Bacterial Enterotoxin by Serum Immunoglobulin A in Response to Mucosal Disease; Infection and Immunity; Aug. 1995; pp. 3166-3173; vol. 63; No. 8.

Jon B. Morris et al; Role of Surgery in Antibiotic-Induced *Pseudomembranous enterocolitis*; The American Journal of Surgery; vol. 160; Nov. 1990; pp. 535-539.

Hiltrud Stubbe et al; Polymeric IgA Is Superior to Monomeric IgA and IgG Carrying the Same Variable Domain in Preventing *Clostridium difficile* Toxin a Damaging of T84 Monolayers; The American Association of Immunologists; 2000; pp. 1952-1960.

Marina S. Morgan et al; The Lancet; vol. 341; Mar. 1993; pp. 701, 702, 1036.

George Triadafilopoulos et al; Differential Effects of *Clostridium difficile* Toxins A and B on Rabbit Ileum; 1987; vol. 93; The American Gastroenterolocial Association; pp. 273-279.

Mark H. Wilcox; Descriptive Study of Intravenous Immunoglobulin for the Treatment of Recurrent *Clostridium difficile* Diarrhoea; Journal of Antimicrobial Chemotherapy; 2004; pp. 882-884.

J.L. Oncley et al; The Separation of the Antibodies, Isoagglutinins, Prothrombin, Plasminogen and B1-Lipoprotein Into Subfractions of Human Plasma; Journal of the American Chemical Society; Feb. 1949; vol. 71; No. 2.

* cited by examiner

TREATMENT OF CELIAC DISEASE WITH IGA

CROSS REFERENCE TO RELATED APPLICATIONS

This application is a continuation-in-part of U.S. patent application Ser. No. 12/138,758 filed Jun. 13, 2008, now U.S. Pat. No. 8,021,645; which in turn is a continuation-in-part of U.S. patent application Ser. No. 11/851,606 filed Sep. 7, 2007, now U.S. Pat. No. 7,794,721; which in turn is a continuation-in-part of U.S. patent application Ser. No. 11/839,781 filed Aug. 16, 2007, now U.S. Pat. No. 7,597,891; which in turn is a continuation-in-part of U.S. patent application Ser. No. 11/610,154 filed Dec. 13, 2006 now abandoned. The contents of these applications are hereby incorporated by reference.

FIELD OF THE INVENTION

This invention relates in general to processes for the treatment of food intolerance, and food allergy with orally administered immunoglobulin A (IgA), including secretory IgA, compositions administered in the form of pharmaceutical compositions.

BACKGROUND OF THE INVENTION

Food intolerance includes, but is not limited to, food protein enteropathy and food protein enterocolitis/proctitis (G. Vighi, et al 2008, Caubet et al 2011). Irritable bowel syndrome is sometimes caused by food intolerance.
The symptoms of irritable bowel syndrome can vary significantly from person to person. A partial listing of irritable bowel syndrome symptoms includes:
  Abdominal pain
  Abdominal distention, bloating, gas, indigestion
  Constipation
  Diarrhea, chronic or occasional
  Food allergy is most often attributed to IgE antibodies with antigenic specificity for specific foods (Granato and Piguet 1986; Wang et al 2010). Foods normally induce local intestinal mucosal production of IgA and IgM (Shimoda et al 1999). Food intolerance and allergy are associated with deficiency in IgA (Walker et al 1999, Harrison et al 1976). It has been hypothesized that food antigen IgA may competitively bind to food antigens, and thereby protect the subject from reacting to that food with an allergic response (Possin et al 2010). Food antigen specific IgA is found in the blood plasma (Vojdani 2009, Trajkovski 2008). Food allergy is associated with a relative decrease in food antigen specific IgA in the intestines (Frossard C P at al 2004). Application of antigen-specific IgA to the respiratory mucosa in mice prevents increased airway hyperreactivity in allergic asthma (Schwarze et al 1998; U.S. Pat. No. 5,670,626). Ulcerative colitis is a chronic inflammation of the large intestine. There is decreased mucosal IgA in the intestinal mucosa of patients with ulcerative colitis (Cicalese et al 1995). Food antigen challenge in the presence of Staphylococcal enteroxin B has been shown to induce ulcerative colitis in a mouse disease model (Yang 2005). Non-IgE mediated food intolerance is also known to exist and be most common in infants and young children due to ingested dietary proteins such as those found in cow's milk and soy protein creating profound discomfort. While non-IgE mediated food allergy is rarely life threatening, it can cause significant morbidity in rapidly growing infants and young children. (Jyonouchi, 2008).

The prior art failed to explore orally administered IgAs or IgMs as a potential medicament for the treatment of food allergy and food intolerance.
Thus, there exists a need for an IgA therapeutic or an IgM therapeutic for the treatment of food allergy and food intolerance. There also exists a need to provide such a therapeutic in a dosing form well suited for treating an affected subject.

SUMMARY OF THE INVENTION

A process is provided for inhibiting symptoms of food allergy or food intolerance in a subject that includes the oral administration of an IgA or an IgM. to the subject suffering from food allergy or food intolerance an IgA or an IgM. When administered in a therapeutic quantity based on the subject characteristics and the type of IgA or IgM, symptoms of food allergy or food intolerance in that subject are inhibited. Even non-secretory forms of IgA and IgM are effective when administered orally. The administered immunoglobulin is readily formed from monoclonal or polyclonal sources. Recombinant forms of the immunoglobulins are also operative herein. When the immunoglobulin is IgA, the IgA is readily administered in a monomeric, dimeric, or polymeric form that optionally includes secretory component. When the. immunoglobulin is IgM, the IgM is readily administered in a monomeric, or pentameric form that optionally includes secretory component.

DETAILED DESCRIPTION OF THE PREFERRED EMBODIMENTS

The present invention has utility as a treatment for food intolerance, irritable bowel syndrome and ulcerative colitis as well as food allergy. The process includes treatment with monoclonal- or polyclonal-IgAs that are monomeric, dimeric or polymeric; and/or monoclonal- or polyclonal-IgM that are monomeric, pentameric and/or secretory. While monomeric IgA is susceptible to gastrointestinal degradation it has been surprisingly found that monomeric immunoglobulin maintains some antibody function after oral administration (Kelly C et al 1997) Because of its resistance to degradation in the gastrointestinal tract, secretory IgA and secretory IgM are generally effective at lower doses. Immunoglobulins have minimal side effects because they are naturally present in the gastrointestinal tract. Dimeric IgA and pentameric IgM according to the present invention may be bound to secretory component in order to mimic secretory IgA and secretory IgM endogenous to the subject. Alternatively they may be administered without bound secretory component.
As used herein, "food allergy" is defined to include IgE and non-IgE mediated allergy and intolerance.
As used herein, a "subject" is defined as a humans.
As the present invention uses an immunoglobulin rather than a metabolic or immunological inhibitor, an effective treatment is provided which does not disturb the body's metabolism.
Allergens that induce food allergies or food intolerance that are mitigated by the present invention illustratively include those allergens found in milk; peanuts; tree nuts, such as cashews and hazelnuts; cauliforates such as cauliflower and broccoli, gluten containing grain crops such as wheat, barley and rye; cheese; eggs; shellfish such as mollusks and crusteaceans; fish; and fruits such as strawberries, bananas, and tomatoes.
The following description of the preferred embodiment(s) is merely exemplary in nature and is in no way intended to limit the invention, its application, or uses.

IgAs and IgMs in various forms including monoclonal- or polyclonal-IgAs that are monomeric, dimeric or polymeric; and monoclonal- or polyclonal-IgMs that are secretory or pentameric are all known to the art, as evidenced for example, by the references incorporated herein.

In one embodiment, the invention provides a process for medical treatment of humans involving the oral administration of secretory IgA which can be derived from a number of sources. One such source for the IgA is pooled human plasma following Cohn cold ethanol fractionation to produce fraction III precipitate as performed by those of skill in the art of protein separation. IgA byproduct is further purified by adsorption onto an ion exchange medium in neutral or slightly acidic conditions as performed by those of skill in the art of protein purification. Another source for the IgA is recombinant IgA produced from a hybridoma or a transgenic plant.

A more detailed description of isolation of an IgA component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted byproduct. According to the invention, this unwanted IgA following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the dimeric and polymeric IgA byproduct during the manufacture of intravenous immunoglobulin. From 4% to 22% of plasma IgA is dimeric and polymeric IgA (Delacroix et al. 1981; Delacroix et al. 1983). The resulting dimeric and polymeric IgA-J chains are purified.

In a preferred embodiment, the compositions of the invention contain, in addition to the IgA component, recombinant secretory component. Human secretory component can be produced by recombinant techniques as described in Crottet et al., Biochem. J. 1999; 341:299-306. The resulting dimeric IgA is further coupled to recombinant secretory component. In a preferred embodiment, the coupling is accomplished by forming disulfide bonds under mildly oxidizing conditions. (Jones 1998) Dimeric IgA containing both J chain and secretory component is again purified by ion-exchange and size exclusion chromatography and/or ultrafiltration as described in Lullau et al., J. Biol. Chem. 1996; 271:16300-16309, Corthesy, Biochem. Soc. Trans. 1997; 25:471-475, and Crottet et al., Biochem. J. 1999; 341:299-306, as performed by those of skill in the art of protein purification. Purified dimeric and polymeric IgA containing secretory component is optionally stabilized for example by the addition of human serum albumin to a final concentration of 5%. The presence of the human J chains and secretory component in the compositions of the invention leads to doses of immunoglobulin A which are more physiologically effective than compositions without such components.

Dimeric IgA contains two IgA monomers plus J chain.

The secretory IgA antibodies may be administered alone as a liquid or solid, preferably in a solid powder form and preferably in admixture with a carrier to form a pharmaceutical composition such as a tablet, capsule or suppository.

Since preferred methods of administration are oral with solid oral dosage forms such as tablets and capsules being especially preferred, or enteric installation. These are prepared according to conventional methods known those skilled in the art. The secretory IgA antibodies may also be combined with other pharmaceutically acceptable carriers such as various liquids, proteins or oils which may also provide additional nutritional and/or pharmaceutical benefits. Remington Science and Practice of Pharmacy, $20^{th}$ ed. (2000).

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged residence in the intestinal lumen of the IgA or IgM can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385,078; 4,518,433; and 4,556,552.

They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Since the effect of the IgA and IgM antibodies is dependent on their reaching the small intestine, preferred tablets or capsules are enteric coated. Alternatively, the active IgA and IgM antibodies can themselves be microencapsulated prior to formulation. Preparation of microcapsules of IgA and IgM antibody as well as preparation of enteric coated tablets or capsules can be achieved by conventional methods as detailed above.

It is appreciated that the therapeutic amount of IgA or IgM depends on the form thereof, with forms subject to gastrointestinal degradation requiring larger doses. Typically amounts of IgA or IgM from about 0.005 mg to 50 grams per day are used and preferably, 1 mg to 40 grams per day. Generally, secretory IgA or IgM are each independently effective as a treatment when provided to the patient at about 1 gram per day. Forms of IgA or IgM that are prone to gastrointestinal degradation are typically effective in doses increased by at least 80% relative to secretory forms. For example, about 5 grams of secretory IgA could be given to a subject per day in a single dose or in divided doses 3 to 4 times per day. Preferably, multiple doses are administered with meals likely containing food allergens. It is appreciated that a physician can readily adjust the doses of the IgA or IgM to be administered based on the subject's response to treatment. Many factors are considered in dose adjustments. Dosages of secretory IgA or secretory IgM for adult humans envisioned by the present invention and considered to be therapeutically effective will range from between about 5 mg to 50 g. However, it is to be understood that doses can readily be adjusted to provide appropriate amounts of the IgA antibody to any subject, including children.

The present invention also provides a process for medical treatment of humans involving the oral administration of monomeric IgA which can be derived from pooled human plasma or monoclonal IgA which can be derived by hybridoma technology (B Cell Design, Limoge, France).

The present invention also provides a process for medical treatment of humans involving the oral administration of secretory IgM which can be derived from pooled human plasma following Cohn cold ethanol fractionation to produce fraction III precipitate as performed by those of skill in the art of protein separation as described above. IgM byproduct is further purified by adsorption onto an ion exchange medium in neutral or slightly acidic conditions as performed by those of skill in the art of protein purification. Another source for the IgM is recombinant IgM produced from a hybridoma.

The invention is further described by reference to the following detailed examples, wherein the processologies are as described below. These examples are not meant to limit the scope of the invention that has been set forth in the foregoing description. Variations within the concepts of the invention are apparent to those skilled in the art.

Example 1

Monoclonal monomeric IgA is obtained from hybridoma technology. The monoclonal IgA is stabilized by the addition of human serum albumin to a final concentration of 5% and encapsulated. The final solution is adjusted to a therapeutic dose of 5 mg IgA daily. The IgA is administered to a person suffering with irritable bowel disease. One day after initiation of treatment, the irritable bowel syndrome sufferer eats the food to which he/she is sensitive without inducing any symptoms of intestinal dysfunction.

Example 2

The monoclonal IgA per Example 1 is administered to a person suffering with food allergy. While receiving treatment the food allergy sufferer eats the allergenic food without inducing any symptoms of an allergic reaction.

Example 3

The process of Example 2 is repeated with the IgA administered with an enteric, encapsulating coating and a lower daily dose of 2 mg to achieve a similar result.

Example 4

The process of Examples 2 is repeated with monoclonal IgA replaced with polyclonal IgA that is obtained from pooled human plasma following Cohn cold ethanol fractionation to produce fraction III precipitate. IgA is further purified by adsorption onto an ion exchange medium in neutral or slightly acidic conditions. IgA-J chain dimers and polymers are purified. IgA-J chain dimers and polymers are then further coupled to recombinant secretory component again by disulfide bonding in mildly oxidizing conditions, preferably at a molar ratio of secretory component to IgA-J chain dimers and polymers of 1:1. IgA containing both J chain and secretory component is again purified. Purified IgA containing J chain and secretory component is stabilized by the addition of human serum albumin to a final concentration of 5%. The final solution of secretory IgA is adjusted to a therapeutic dose of 5 mg IgA and is administered to a person suffering with food allergy to eggs. One month after initiation of treatment the food allergy sufferer eats 50 grams of egg without inducing any symptoms of an allergic reaction.

Example 5

The process of Example 4 is repeated with a person suffering from a food intolerance to cauliforates to achieve a similar result.

Example 6

The process of Example 4 is repeated with a person suffering from ulcerative collitis to achieve a similar result.

Example 7

The process of Example 4 is repeated with a person suffering from a food allergy to strawberries to achieve a similar result.

Example 8

The process of Example 4 is repeated with a person suffering from irritable bowel syndrome to achieve a similar result.

Example 9

The process of Example 4 is repeated with a person suffering from a peanut allergy to achieve a similar result.

Example 10

The process of Example 4 is repeated with monoclonal IgA replaced with polyclonal IgM that is obtained from pooled human plasma following Cohn cold ethanol fractionation to produce fraction III precipitate. IgM is further purified by adsorption onto an ion exchange medium in neutral or slightly acidic conditions. IgM-J chain pentamers are purified. IgM-J chain pentamers are then further coupled to recombinant secretory component again by disulfide bonding in mildly oxidizing conditions, preferably at a molar ratio of secretory component to IgM-J chain pentamers of 1:1. IgA containing both J chain and secretory component is again purified. Purified IgM containing J chain and secretory component is stabilized by the addition of human serum albumin to a final concentration of 5%. The final solution is adjusted to a therapeutic dose of 10 mg IgM. The IgM is administered to a person suffering with food allergy. One month after to initiation of treatment the food allergy sufferer eats the allergenic food without inducing any allergic symptoms.

Examples 10-14

Examples 5-9 are repeated with monoclonal IgA replaced with polyclonal IgM per Example 10 to achieve like results.

REFERENCES

Berzofsky J. A., Berkower I. J., Epstein S. L., Monoclonal Antibodies in Chapter 12, Antigen-Antibody Interactions and Monoclonal Antibodies, pp. 455-465 in Fundamental Immunology, Third Edition, W. E. Paul (ed), Raven Press, NY 1993. Berzofsky et al., Fundamental Immunology, Third Edition, 1993, pp 455-462.

Cicalese L, Duerr R H, Nalesnik M A, Heeckt P F, Lee K K, Schraut W H. Decreased mucosal IgA levelsin ileumof patients with chronic ulcerative colitis. Dig Dis Sci. 1995 April; 40(4):805-11.

Cohn E. J., Strong L. E., Hughes W. L., Jr., Mulford D. J., Ashworth J. N., Melin M., Taylor H. L., Preparation and Properties of Serum and Plasma Proteins IV. A System for the Separation into Fractions of the Protein and Lipoprotein Components of Biological Tissues and Fluids, J. Am. Chem. Soc. 1946; 68; 459-475.

Corthesy B., Recombinant Secretory IgA for Immune Intervention Against Mucosal Pathogens, Biochem. Soc. Trans. 1997, 25; 471-475.

Crottet P., Cottet S., Corthesy B., Expression, Purification and Biochemical Characterization of Recombinant Murine Secretory Component, A Novel Tool in Mucosal Immunology, Biochem. J. 1999, 341; 299-306.

Caubet J C, Nowak-Wgrzyn A. Current understanding of the immune mechanisms of food protein-induced enterocolitis syndrome. Expert Rev Clin Immunol. 2011 May; 7(3): 317-27.

Delacroix D. L., Hodgson H. J., McPherson A., Dive C., Vaerman J. P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August; 70(2):230-41

Delacroix D. L., Elkom K. B., Geubel A. P., Hodgson H. F., Dive C., Vaerman J. P. Changes in size, subclass, and metabolic properties of serum immunoglobulin A in liver diseases and in other diseases with high serum immunoglobulin A. J. Clin. Invest. 1983 February; 71(2):358-67.

Frossard C P, Hauser C, Eigenmann P A. Antigen-specific secretory IgA antibodies in the gut are decreased in a mouse model of food allergy. J Allergy Clin Immunol. 2004 August; 114(2):377-82.

Granato D A, Piguet P F. A mouse monoclonal IgE antibody anti bovine milk beta-lactoglobulin allows studies of allergy in the gastrointestinal tract. Clin Exp Immunol. 1986 March; 63(3):703-10.

Harrison M, Kilby A, Walker-Smith J A, France N E, Wood C B. Cows' milk protein intolerance: a possible association with gastroenteritis, lactose intolerance, and IgA deficiency. Br Med J. 1976 Jun. 19; 1(6024):1501-4.

Jones R. M. L., Schweikart F., Frutiger S., Jaton J-C., Hughes G. J. Thiol-disulfide redox buffers maintain a structure of immunoglobulin A that is essential for optimal in vitro binding to secretory component. Biochimica et Biophysica Acta 1998; 1429:265-274.

Harumi Jyonouchi Non-IgE Mediated Food Allergy. *Inflammation & Allergy—Drug Targets,* 2008, 7, 000-000.

Kelly C P, Chetham S, Keates S, Bostwick E F, Roush A M, Castagliuolo I, LaMont J T, Pothoulakis C. Survival of Anti-*Clostridium difficile* Bovine Immunoglobulin Concentrate in the Human Gastrointestinal Tract. Antimicrob Agents Chemother. 1997 February; 41(2):236-41.

Kohler G., Milstein C., Continuous Cultures of Fused Cells Secreting Antibody of Predetermined Specificity, Nature 1975; 256; 495-497.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Oncley J. L., Melin M., Richert D. A., Cameron J. W., Gross P. M., Jr., The Separation of the Antibodies, Isoagglutinins, Prothrombin, Plasminogen and β1-Lipoprotein into Subfractions of Human Plasma. J. Am. Chem. Soc. 1949; 71:541-550.

Possin M E, Morgan S, DaSilva D F, Tisler C, Pappas T E, Roberg K A, Anderson E, Evans M D, Gangnon R, Lemanske R F, Gern J E. The relationships among immunoglobulin levels, allergic sensitization, and viral respiratory illnesses in early childhood. Pediatr Allergy Immunol 2010: 21: 990-996.

J Schwarze J, Cieslewicz G, Joetham A, L Sun L K, Sun W N, Chang T W, Hamelmann E, W. Gelfand E W. Antigen-specific Immunoglobulin-A Prevents Increased Airway Responsiveness and Lung Eosinophilia after Airway Challenge in Sensitized Mice. Am J Resp Crit Care Med 1998; 158:519-525.

Shimoda M, Inoue Y, Azuma N, Kanno C. Local antibody response in Peyer's patches to the orally administered dietary protein antigen. Biosci Biotechnol Biochem. 1999 December; 63(12):2123-9.

Strong L. E., Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, NY 1963, pp. 576-602.

Symersky J., Novak J., McPherson D. T., DeLucas L., Mestecky J. Expression of the recombinant human immunoglobulin J chain in Escherichia coli. Mol. Immunol. 2000; 37:133-140.

Trajkovski V, Ajdinski L, Spiroski M. Plasma concentration of immunoglobulin classes and subclasses in children with autism in the Republic of Macedonia: retrospective study. Croat Med J. 2004 December; 45(6):746-9.

Vighi G, Marcucci F, Sensi L, G. Di Cara G, Frati F. Allergy and the gastrointestinal system. *Clinical and Experimental Immunology*, 153 (Suppl. 1): 3-6, 2008.

Vojdani A. Detection of IgE, IgG, IgA and IgM antibodies against raw and processed food antigens. Nutr Metab (Lond). 2009 May 12; 6:22

Walker A M, Kemp A S, Hill D J, Shelton M J. Features of transient hypogammaglobulinaemia in infants screened for immunological abnormalities. Arch Dis Child. 1994 March; 70(3): 183-186.

Wang M, Takeda K, Shiraishi Y, Okamoto M, Dakhama A, Joetham A, Gelfand E W. Peanut-induced intestinal allergy is mediated through a mast cell-IgE-FcepsilonRI-IL-13 pathway. J Allergy Clin Immunol. 2010 August; 126(2): 306-16, 316.e1-12.

Yang P-C, Wang C-S, An Z-Y. A murine model of ulcerative colitis: induced with sinusitis-derived superantigen and food allergen. BMC Gastroenterology 2005, 5:6.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof The following claims, including all equivalents thereof, are intended to define the scope of the invention.

The invention claimed is:

1. A process for inhibiting symptoms of food allergy in a subject comprising:
    administering orally to the subject suffering from food allergy a purified IgA; and
    allowing sufficient time for said purified IgA to inhibit symptoms of food allergy in that subject wherein an allergen that induces the food allergy is present in food selected from the group consisting of: a milk, a peanut, a tree nut, a cauliforate, a gluten containing grain crop, a cheese, an egg, a shellfish, a fish; and a fruit.

2. The process of claim 1, wherein said IgA is administered and is polyclonal or monoclonal.

3. The process of claim 2, wherein said IgA is monomeric.

4. The process of claim 2, wherein said IgA is dimeric.

5. The process of claim 2, wherein said IgA is polymeric.

6. The process of claim 2, wherein said IgA is recombinant.

7. The process of claim 4 further comprising IgA bound to secretory component.

8. The process of claim 1 wherein said IgA is administered as a tablet or a capsule.

9. The process of claim 1 further comprising microencapsulating said IgA prior to said administrating.

10. A process for inhibiting symptoms of food intolerance in a subject comprising:
    administering orally to the subject suffering from food intolerance a purified IgA; and
    allowing sufficient time for said purified IgA to inhibit symptoms of food intolerance in that subject wherein a food that induces the food intolerance is present in food selected from the group consisting of: a milk, a peanut, a tree nut, a cauliforate, a gluten containing grain crop, a cheese, an egg, a shellfish, a fish; and a fruit.

11. The process of claim 10 wherein food intolerance causes or exacerbates irritable bowel syndrome.

12. The process of claim 10, wherein said IgA is administered and is polyclonal or monoclonal.

13. The process of claim 10, wherein said IgA is monomeric.

14. The process of claim 10, wherein said IgA is dimeric.

15. The process of claim 10, wherein said IgA is polymeric.

16. The process of claim 10, wherein said IgA is recombinant.

17. The process of claim 14 further comprising IgA bound to secretory component.

18. The process of claim 10 wherein said IgA is administered as a tablet or a capsule.

19. The process of claim 10 further comprising microencapsulating said IgA prior to said administration.

* * * * *